US009949877B2

(12) United States Patent
Rubinchik et al.

(10) Patent No.: US 9,949,877 B2
(45) Date of Patent: Apr. 24, 2018

(54) PHOTODYNAMIC THERAPY LASER

(71) Applicant: Valeant Pharmaceuticals International, Inc., West, Laval, Quebec (CA)

(72) Inventors: Valery Rubinchik, Richmond (CA); Charles Richard Kjellbotn, Parksville (CA); Greg Heacock, Maple Valley, WA (US); Louise Culham, Maple Valley, WA (US); Wes A. Williams, Gig Harbor, WA (US)

(73) Assignee: Valeant Pharmaceuticals International, Inc. (CA)

( * ) Notice: Subject to any disclaimer, the term of this patent is extended or adjusted under 35 U.S.C. 154(b) by 35 days.

(21) Appl. No.: 14/872,248

(22) Filed: Oct. 1, 2015

(65) Prior Publication Data

US 2016/0074222 A1 Mar. 17, 2016

Related U.S. Application Data

(62) Division of application No. 13/426,470, filed on Mar. 21, 2012, now Pat. No. 9,211,214.

(51) Int. Cl.
*A61N 5/067* (2006.01)
*A61F 9/008* (2006.01)
(Continued)

(52) U.S. Cl.
CPC .......... *A61F 9/00821* (2013.01); *A61N 5/062* (2013.01); *A61B 2018/2035* (2013.01);
(Continued)

(58) Field of Classification Search
CPC .. A61N 5/06; A61N 5/062; A61N 2005/0631; A61N 2005/0632;
(Continued)

(56) References Cited

U.S. PATENT DOCUMENTS 4,917,486 A * 4/1990 Raven ..................... A61F 9/008
351/221
5,095,030 A 1/1992 Levy et al.
(Continued)

FOREIGN PATENT DOCUMENTS

EP 0 075 860 A2 4/1983
EP 0 280 414 A1 8/1988
(Continued)

OTHER PUBLICATIONS

International Search Report for International Application No. PCT/US2013/033309 International Searching Authority, United States, dated Jun. 14, 2013.
(Continued)

*Primary Examiner* — Ahmed Farah
(74) *Attorney, Agent, or Firm* — Andrew J. Anderson, Esq.; Harter Secrest & Emery LLP

(57) ABSTRACT

A laser system including: a laser source operable to emit a first laser beam having a first operating wavelength and a second laser beam having a second operating wavelength; a fiber optic cable to guide and homogenize the first and second laser beams; an expander to increase the diameter of the first and second laser beams; a cylinder to guide the first and second laser beams and limit respective diameters of the first and second laser beams, wherein the cylinder is positioned after the expander on an optical path of the laser beam; a first optical system to collimate the first and second laser beams, wherein the optical system is positioned after the cylinder on the optical path of the first and second laser beams; a spot-size selector comprising a plurality of apertures, wherein the spot-size selector is positioned after the first optical system on the optical path of the first and second laser beams; and a second optical system to focus the first and second laser beams on a tissue of the patient.

7 Claims, 16 Drawing Sheets

(51) Int. Cl.
*A61N 5/06* (2006.01)
*A61B 18/20* (2006.01)

(52) U.S. Cl.
CPC . *A61F 9/00823* (2013.01); *A61F 2009/00844* (2013.01); *A61F 2009/00863* (2013.01); *A61N 2005/063* (2013.01); *A61N 2005/067* (2013.01); *A61N 2005/0643* (2013.01); *A61N 2005/0667* (2013.01)

(58) Field of Classification Search
CPC .... A61N 2005/0643; A61N 2005/0664; A61N 2005/0667; A61N 2005/067; A61F 9/008; A61F 9/008221; A61F 2009/00861; A61F 2009/0083
USPC ............ 607/88–92; 606/4–6, 10–14, 16–18; 128/898
See application file for complete search history.

(56) References Cited

U.S. PATENT DOCUMENTS

| | | | |
|---|---|---|---|
| 5,098,426 A | 3/1992 | Sklar et al. | |
| 5,171,749 A | 12/1992 | Levy et al. | |
| 5,305,759 A | 4/1994 | Kaneko et al. | |
| 5,311,224 A | 5/1994 | Enomoto | |
| 5,442,487 A | 8/1995 | Mizuno | |
| 5,707,608 A | 1/1998 | Liu | |
| 5,756,541 A | 5/1998 | Strong et al. | |
| 5,770,619 A | 6/1998 | Richter et al. | |
| 5,798,349 A | 8/1998 | Levy et al. | |
| 5,843,070 A | 12/1998 | Cambier et al. | |
| 6,074,666 A | 6/2000 | Desai et al. | |
| 6,676,654 B1* | 1/2004 | Balle-Petersen ..... | A61N 5/0616 606/11 |
| 6,868,236 B2 | 3/2005 | Wiltsey et al. | |
| 6,932,807 B1 | 8/2005 | Tomita et al. | |
| 8,523,849 B2* | 9/2013 | Liu ...................... | A61B 18/203 606/9 |
| 9,005,262 B2* | 4/2015 | Liu ...................... | A61B 18/203 606/9 |
| 2002/0068925 A1* | 6/2002 | Murakami ............. | A61F 9/008 606/4 |
| 2006/0127481 A1 | 6/2006 | Kataoka et al. | |
| 2008/0027418 A1* | 1/2008 | Berry ..................... | A61F 9/008 606/5 |
| 2008/0243108 A1 | 10/2008 | Murakami et al. | |
| 2009/0275929 A1 | 11/2009 | Zickler | |
| 2011/0034973 A1* | 2/2011 | Wang .................... | A61B 18/22 607/89 |
| 2013/0043392 A1* | 2/2013 | Mildren .................. | H01S 3/30 250/341.1 |
| 2013/0211391 A1* | 8/2013 | BenYakar ............. | A61B 18/20 606/10 |
| 2014/0005756 A1* | 1/2014 | Liu ...................... | A61B 18/203 607/90 |
| 2016/0089269 A1* | 3/2016 | Horvath .............. | A61F 9/00825 606/5 |

FOREIGN PATENT DOCUMENTS

| | | |
|---|---|---|
| EP | 0 402 017 A2 | 12/1990 |
| EP | 1 210 922 A1 | 6/2002 |
| WO | 2011/143663 A2 | 11/2011 |

OTHER PUBLICATIONS

European Search Report dated Nov. 12, 2015 (4 pages).

* cited by examiner

| Aperture | System Magnification | Spot size (mm) | | |
|---|---|---|---|---|
| | | At Real Image (1.0 mag) | Volk Area Centralis (1.06 mag) | Mainster Wide Field (1.47 mag) |
| 0.50 | 0.786 | 0.393 | 0.42 | 0.58 |
| 1.20 | 0.786 | 0.943 | 1.00 | 1.39 |
| 1.68 | 0.786 | 1.321 | 1.40 | 1.94 |
| 2.16 | 0.786 | 1.698 | 1.80 | 2.50 |
| 2.58 | 0.786 | 2.028 | 2.15 | 2.98 |
| 3.00 | 0.786 | 2.358 | 2.50 | 3.47 |
| 3.42 | 0.786 | 2.689 | 2.85 | 3.95 |
| 3.84 | 0.786 | 3.019 | 3.20 | 4.44 |
| 4.26 | 0.786 | 3.349 | 3.55 | 4.92 |
| 4.68 | 0.786 | 3.679 | 3.90 | 5.41 |
| 5.10 | 0.786 | 4.009 | 4.25 | 5.89 |
| 5.52 | 0.786 | 4.340 | 4.60 | 6.38 |

Figure 13

LC LASER SOFTWARE PROCESS FLOW

PHOTODYNAMIC THERAPY LASER

FIELD OF THE INVENTION

This invention relates generally to lasers, and more particularly to photodynamic therapy laser systems which are compact, portable and easier to use in a treatment facility.

BACKGROUND

Photodynamic therapy (PDT) is a non-invasive medical procedure used for the treatment of various diseases. PDT involves the administration of a photosensitizing compound that concentrates around a portion of tissue. Thereafter the tissue that is concentrated with the photosensitizing compound is irradiated. The target tissue containing a sufficiently high concentration of the photosensitizing compound selectively absorbs the light which induces impairment or destruction of the immediately surrounding cells.

One disease treated with PDT is wet age-related macular degeneration. Age-related macular degeneration results in the loss of vision in the macula due to damage in the retina. The wet (or excudative) form of age-related macular degeneration occurs when blood vessels spread from the choroid behind the retina. This abnormal blood vessel growth can cause detachment of the retina. The detachment of the retina can be avoided by preventing the spread of abnormal blood vessel growth. The spread is prevented by irradiating a photosensitizing compound in a tissue that causes impairment or destruction of the surrounding cells through a cytotoxic effect. A method of PDT is described in U.S. Pat. No. 5,756,541, the entirety of which is incorporated by reference.

Typically, photosensitizing agents such as Visudyne® are used to treat the wet form of age-related macular degeneration. Visudyne® is discussed in U.S. Pat. Nos. 5,171,749, 5,095,030, 5,707,608, 5,770,619, 5,798,349, and 6,074,666, the entireties of which are incorporated by reference. Visudyne® is administered intravenously for approximately ten minutes. After approximately fifteen minutes, the treatment site is activated with laser light having a wavelength of approximately 689 nm at 150-600 mW/m$^2$. As known to those skilled in the art, verteporfin is the generic form or equivalent of Visudyne There are several laser systems in the prior art to deliver laser light such as Lumenis' Opal Photactivator laser console and modified Lumenis LaserLink adapter manufactured by Lumenis, Inc., Zeiss' VISULAS 690s laser and VISULINK® PDT adapter manufactured by Carl Zeiss Meditec Inc., and Quantel's Activis laser console and ZSL30 ACT™, ZSL120 ACT™, Ceralas™ I laser system and Ceralink™ Slit Lamp Adaptor manufactured by Biolitec, Inc. and HSBMBQ ACT™ slit lamp adapters distributed by Quantel Medical. These prior art laser systems have bulky control panels and are expensive and increase the costs of PDT for wet age-related macular degeneration.

Therefore, there is a need in the art for a PDT laser system to be used for treating wet age-related macular degeneration, central serous chorioretinopathy (CSC) or polypoidal chorodial vasculopathy (PCV), (subfoveal occult or classical) coroidal neovasculization (CNV), and other similar diseases which is compact, portable, easier to use in a treatment facility, and economical to manufacture.

SUMMARY OF THE INVENTION

The presently disclosed embodiments are directed to solving issues relating to one or more of the problems presented in the prior art, as well as providing additional features that will become readily apparent by reference to exemplary embodiments in the following detailed description when taken in conjunction with the accompanying drawings.

According to one embodiment, a treatment beam and an aiming beam is generated from a single laser head. The beams are transmitted through a fiber optic cable which provides mode-mixing for spot uniformity. The laser light is then expanded and collimated. The collimated laser light is propagated through an aperture wheel that is configured to set a spot size. The light from the aperture wheel is propagated through a lens wherein it is focused from the lens onto a partially reflective mirror. The partially reflective mirror is configured to reflect a high percentage of the treatment beam and partially reflect a smaller percentage of the aiming beam into a patient's eye.

In a further embodiment, light from the partially reflective mirror is propagated to the treatment site wherein the light beam that irradiates the treatment site has a top hat profile of fluence for each desired spot size.

In a further embodiment, the laser head is designed to run at a higher power output but actually run at a lower power output to generate less heat.

In a further embodiment, a tonometer post allows the optical system to be removably attachable to a slit lamp microscope.

In a further embodiment, heat from the laser head is dissipated in a heat sink. In a further embodiment, the heat sink is coupled to a fin array. The fin array may be coupled to the heat sink with a heat pipe.

In one embodiment, the invention provides a laser system configured for administering therapy to a patient. The laser system includes: a laser source operable to emit a first laser beam having a first operating wavelength and a second laser beam having a second operating wavelength; a fiber optic cable to guide and homogenize the first and second laser beams; an expander to increase the diameter of the first and second laser beams; a cylinder to guide the first and second laser beams and limit respective diameters of the first and second laser beams, wherein the cylinder is positioned after the expander on an optical path of the laser beam; a first optical system to collimate the first and second laser beams, wherein the optical system is positioned after the cylinder on the optical path of the first and second laser beams; a spot-size selector comprising a plurality of apertures, wherein the spot-size selector is positioned after the first optical system on the optical path of the first and second laser beams; a second optical system to focus the first and second laser beams on a tissue of the patient, wherein the second optical system is positioned after the spot-size selector on the optical path of the first and second laser beams; and an optical filter configured to partially reflect the first and second laser beams, wherein the optical filter is positioned after the second optical system on the optical path of the laser beams, wherein the optical filter reflects a first percentage of the first laser beam and second percentage of the second laser beam, and wherein the first percentage is greater than the second percentage.

In another embodiment, a laser system configured for administering therapy to a patient, includes: a laser source operable to emit a first laser beam operating a first wavelength and a second laser beam operating at a second wavelength, wherein the laser source operates at 1.5 watts or less; a passive cooling system, wherein the passive cooling system comprises a heat pipe, a heat sink, and a fin array; a fiber optic cable coupled to the laser source and configured to guide and homogenize the first and second laser beams; a first optical system coupled to the fiber optic cable and configured to increase the diameter of and collimate the first and second laser beams; a spot-size selector coupled to the first optical system and comprising a plurality of apertures; and a second optical system coupled to the spot-size selector and configured to focus the laser beam on an eye tissue of the patient.

In a further embodiment, a laser system configured for administering therapy to a patient, includes: a laser source operable to emit a first laser beam having a first operating wavelength and a second laser beam having a second operating wavelength; a fiber optic cable to guide and homogenize the first and second laser beams, wherein the fiber optic cable has a diameter of about 350 to 450 microns and a length of about 200 to 300 millimeters; a first optical system coupled to the fiber optic cable and configured to increase the diameter of and collimate the first and second laser beams; a spot-size selector coupled to the first optical system and comprising a plurality of apertures, wherein the spot-size selector is positioned after the first optical system on the optical path of the first and second laser beams, and the fiber optic cable is the only fiber optic cable between the laser source and the spot-size selector; and a second optical system coupled to the spot-size selector and configured to focus the laser beam on an eye tissue of the patient.

In another embodiment, a method of activating a photoactive drug administered to a patient intravenously includes: activating the photoactive agent with a first laser beam generated by a laser apparatus, the first laser beam having a first wavelength; generating a second laser beam operating at a second wavelength, wherein the combined power levels of both the first and second laser beams are 1.5 watts or less; passively cooling the laser apparatus by coupling a heat sink to a laser source of the laser apparatus; guiding the first and second laser beams through a fiber optic cable coupled to the laser source, wherein the fiber optic cable homogenizes the first and second laser beams; collimating the first and second laser beams; adjusting a spot-size of the first and second laser beams; and focusing the first and second laser beams on an eye tissue of the patient, wherein at least the first laser beam activates the photoactive drug within the patient's eye tissue to provide therapy to the patient. In a further embodiment, the photo activate agent comprises verteporfin.

In yet another embodiment, a laser system configured for activating a photoactive drug administered to a patient intravenously includes: a laser source operable to emit a first laser beam operating a first wavelength and a second laser beam operating at a second wavelength, wherein the laser source operates at 1.5 watts or less; a passive cooling system, wherein the passive cooling system comprises a heat pipe, a heat sink, and a fin array; a fiber optic cable coupled to the laser source and configured to guide and homogenize the first and second laser beams; a first optical system coupled to the fiber optic cable and configured to increase the diameter of and collimate the first and second laser beams; a spot-size selector coupled to the first optical system and comprising a plurality of apertures; and a second optical system coupled to the spot-size selector and configured to focus the first and second laser beams on an eye tissue of the patient, wherein at least the first laser beam activates the photoactive drug within the patient's eye tissue to provide therapy to the patient. In a further embodiment, the photo activate agent comprises verteporfin.

BRIEF DESCRIPTION OF THE DRAWINGS

Various exemplary embodiments of the invention are described in detail below with reference to the following Figures. The drawings are provided for purposes of illustration only and merely depict exemplary embodiments of the invention. These drawings are provided to facilitate the reader's understanding of the invention and should not be considered limiting of the breadth, scope, or applicability of the invention. It should be noted that for clarity and ease of illustration these drawings are not necessarily drawn to scale.

FIGS. 13 and 14 illustrate some exemplary combinations of aperture size, spot size, and system magnification, in accordance with one embodiment of the invention.

DETAILED DESCRIPTION OF EXEMPLARY EMBODIMENTS

Figure 1:
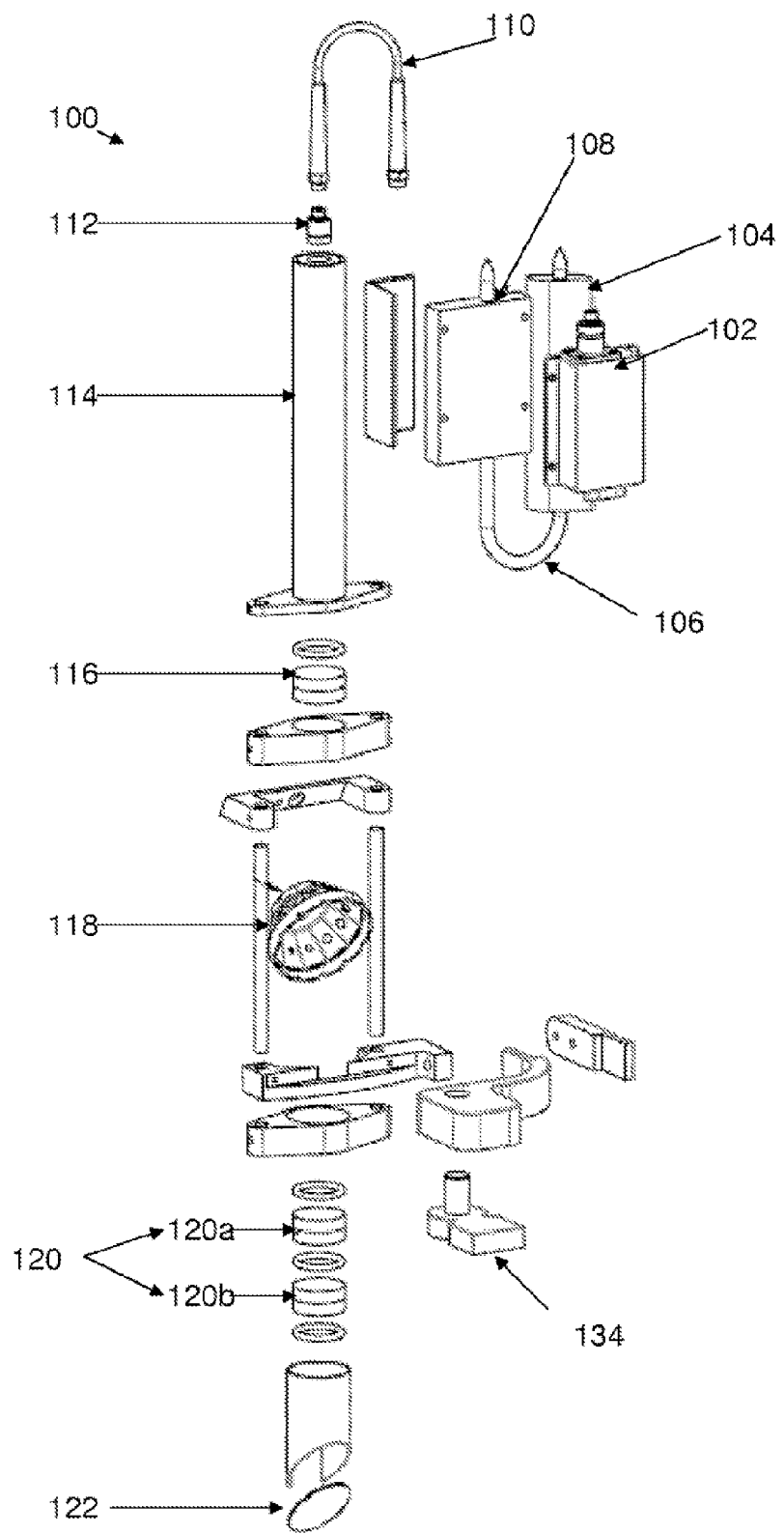
FIG. 1 illustrates exemplary components of a compact PDT laser according to one embodiment of the invention.

The following description is presented to enable a person of ordinary skill in the art to make and use the invention. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described herein and shown, but is to be accorded the scope consistent with the claims.

The word "exemplary" is used herein to mean "serving as an example or illustration." Any aspect or design described herein as "exemplary" is not necessarily to be construed as preferred or advantageous over other aspects or designs.

Reference will now be made in detail to aspects of the subject technology, examples of which are illustrated in the accompanying drawings and tables, wherein like reference numerals refer to like elements throughout.

It should be understood that the specific order or hierarchy of steps in the processes disclosed herein is an example of exemplary approaches. Based upon design preferences, it is understood that the specific order or hierarchy of steps in the processes may be rearranged while remaining within the scope of the present invention. The accompanying method claims present elements of the various steps in a sample order, and are not meant to be limited to the specific order or hierarchy presented.

FIG. 1 illustrates an exploded view of an exemplary PDT laser system 100 wherein each individual component is shown disconnected from the other individual components. Laser light is generated from the laser head 102. The laser head may be obtained commercially (e.g., nLIGHT Pearl™) or may be constructed of any number of laser generation components (e.g., pump diodes, gas lasers). It is understood that any laser design capable of providing two or more coincident beams may be utilized.

The laser head 102 generates a treatment and an aiming beam. According to an exemplary embodiment, the treatment beam has a spot size that is variable from 350 μm to 5000 μm. According to an exemplary embodiment, the laser head 102 can generate fluence rates of 150 mW/cm$^2$, 300 mW/cm$^2$, 450 mW/cm$^2$, and 600 mW/cm$^2$. In further embodiments, contact lens magnification is accounted for when calculating the required fluence rate. In some embodiments, 90% of the treatment beam output power is in the spectral range of 689 nm±3 nm in order to effectively activate a photosynthesizing agent (e.g., Visudyne®). The aiming beam may have a spectral output in the range of 635 nm±10 nm. It should be understood that the invention is not limited to the spot sizes, fluence rates and treatment beam ranges disclosed, and the parameters listed above are for exemplary purposes only.

According to an exemplary embodiment, the circularity (the normalized ratio of the minor to the major axis of an ellipse fitted to the beam output) is greater than 0.870 for all spot sizes. According to a further exemplary embodiment, the beam shall have uniform power distribution throughout.

According to one embodiment, the uniformity sigma is no greater than 20% when defined as the standard deviation of the intensity of the beam image calculated by:

$$\sigma = \sqrt{\frac{\Sigma(P_j - M)^2}{N-1}}$$

where P is the pixel value, M is the mean pixel value and N is the total number of pixels inside the analysis area. According to one embodiment, the beam profile does not deviate from the equation above during treatment.

According to an exemplary embodiment, the laser head 102 provides a light dose of 12.5 J/cm$^2$, 25 J/cm$^2$, 37.5 J/cm$^2$, or 50 J/cm$^2$. The exposure duration can be automatically controlled to deliver a requested light dose at a requested fluence. When the requested dose of light has been delivered, the laser head 102 will automatically shut off.

According to an exemplary embodiment, the diameter and position of the aiming beam is coincident with the treatment beam so that a health care professional can adequately apply the treatment beam to the treatment spot. The output power of the aiming beam is 1 mW or less. According to a further embodiment, the visibility of the aiming beam is adjustable (e.g., from barely visible to maximum visibility). In an exemplary embodiment, the wavelength of the aiming beam is in the range of 625-645 nm.

Unlike prior conventional laser systems, the current invention combines a treatment beam and aiming beam in a single laser head 102, whereby these embodiments of the present invention advantageously allow the laser head 102 to be mounted on a typical optical system rather than as a stand-alone console as provided by conventional laser systems. A further benefit to combining the treatment and aiming beam is a more compact PDT laser system 100, which can be more compact, economical to manufacture, as well as more portable and useable in a treatment facility.

According to an exemplary embodiment, the laser head 102 may be current controlled. A current controlled laser head 102 may be manufactured inexpensively and by controlling the maximum current to the laser, safety is improved. In one embodiment, the laser head 102 may be engineered to operate at a higher power (e.g., 5 W) wherein it is actually run at a lower power (e.g., 1 W or 1.5 W) to reduce heat output and extend useful life.

It is understood that any method of current control may be utilized. For example, current may be controlled by an external foot pedal, a knob, a computer, or any other device known in the art. It is understood that a current control device may be located on the laser head 102. Further, it is understood that the laser head 102 may be voltage controlled (e.g., voltage corresponding to beam intensity) or controlled by digital communication signals.

According to an exemplary embodiment, the laser head 102 can be made to run below specification at 1 to 1.5 W to generate less heat. In one embodiment, the laser head 102 is configured to run at a power level of approximately 325 mW to 750 mW to further reduce heat generation. The lower heat generated allows the laser head 102 to be passively cooled. According to an exemplary embodiment, a heat sink 108 is coupled to the laser head 102. The heat sink 108 is coupled to a heat pipe 106 that transfers heat to a fin array 104. The fin array 104 dissipates the heat into the air. The heat sink 108, heat pipe 106, and fin array 104 may be made of any material known in the art to disperse the heat.

According to one embodiment, the cooling system may utilize working fluid as known in the field of heat transfer in order cool the laser head 102. For example, the heat sink 108, the heat pipe 106, and/or the fin array 104 may be filled with a small quantity of working fluid (e.g., water, acetone, nitrogen, methanol, ammonia, or sodium, etc.). Heat is absorbed by vaporizing the working fluid. The vapor transports heat to the condenser region where the condensed vapor releases heat to a cooling medium. The condensed working fluid is returned to the evaporator by gravity, or by a wick structure on the heat pipe 106 or fin array 104, creating capillary action.

The passive cooling system contributes to reducing the cost of the exemplary PDT laser in a number of ways. First, the passive cooling system is less expensive than active cooling systems of the prior art. The passive cooling system cost less to manufacture, to maintain, and to operate when compared to active cooling systems. Second, the passive cooling system is more compact than active systems, allowing the cooling system to be installed in a housing with the laser, and the housing positioned on known slit lamp microscopes. According to an exemplary embodiment, the heat sink 108 can assist the laser head 102 to keeping the therapeutic wavelength within ±1 nm and the therapeutic energy within 3% of the desired treatment fluence.

According to one embodiment, the laser head 102 has a heat dissipation area of approximately 11.4 cm by 2.86 cm. Therefore, by having ten times or more surface area for heat dissipation could allow the laser head 102 to operate within therapeutic parameters. According to one embodiment, a metal sheet housing may be utilized to dissipate heat of the laser head 102.

According to one embodiment, the heat sink 108, the heat pipe 106, and the fin array 104 provide approximately a 25 times factor increase in surface area for heat dissipation. According to one embodiment, the heat pipe 106 may be utilized to deliver heat to the fin array 104 that can be placed at any convenient location within the instrument enclosure. According to an embodiment, the 32.6 cm$^2$ heat dissipation surface of the laser head 102 is attached to a heat sink 108 in combination with a heat pipe 106 and a fin array 104 wherein the heat distribution structure has a 810 cm$^2$ heat dissipation surface. According to one embodiment, the laser head 102 may be optimally placed near the optical components and the heat may be transferred to a convenient location on or outside of the PDT laser system.

According to an exemplary embodiment, the two laser beams from the laser head 102 are propagated through a fiber optic cable 110. The fiber optic cable 110 has a curve in the Z-axis. This Z-axis curve works as a mode-scrambler. Mode scrambling distributes the optical power in a fiber among all the guided modes. One known scrambling technique is to splice a length of graded-index fiber between two pieces of step-index, but such techniques are expensive and add the complication of fiber alignment. In one embodiment of the present invention, curving the fiber in the Z-axis reduces cost and eliminates the complications of fiber alignment. Further, short fiber optic cable (250 mm, for example) causes rapid coupling between all fiber modes and attenuation of high order modes. The fiber optic cable 110 outputs a uniform output intensity profile and circularity independent of the intensity profile of the laser head 102.

According to an exemplary embodiment, the fiber optic cable 110 is about 250 mm in length and has a diameter of about 400 microns. Given the smaller size of the fiber optic cable 110, it may be positioned on the optical system. Typically, prior art systems had long fiber optic cables connecting a laser head to the slit lamp optical system. Prior art systems suffer from degradation of the fiber optic cable and breakage. Thus, the shorter fiber optic cable 110 of embodiments of the present invention is more robust and more cost efficient.

The uniform light from the fiber optic cable 110 is propagated to a laser beam expander 112 that expands the output light. In one embodiment, the fiber optic cable 110 may connect to a fiber lens (not shown) having 4.5 mm focal length (FL). The expanded light is outputted from the laser beam expander 112 into the light diverger 114 that diverges the light. According to one embodiment, the beam expander 112 may have a lens having a 48 mm FL. In one embodiment, the beam expander 112 comprises a biconcave lens having negative power. A diverging beam propagates the length of the beam expander 112 tube, which provides additional beam divergence to the beam.

The diverged light propagates from the diverger 114 to the collimator 116. The light that is outputted from the collimator 116 is more parallel, relative to the inputted light, in a specific direction and its spatial cross section is smaller. Further, the light exiting the collimator has a substantially uniform fluence. The light is collimated so it may pass through a mechanical device and still provide uniform fluence on the target site.

The fiber optic cable 110, the expander 112, the diverger 114, and the collimator 116 are provided as exemplary embodiments. It is understood that alternative mechanisms in the art or additional components may be utilized to deliver light of a uniform fluence.

The light from the collimator 116 is propagated to the aperture wheel 118. The aperture wheel 118 comprises a series of apertures to set different spot sizes for the treatment beam. The spot sizes may be physically set by a person manually rotating the aperture wheel to the desired spot size. In other embodiments, a motorized system may rotate the wheel after a desired spot size is selected by a user or a computer system. It is envisioned that a plurality of different spot size values may be utilized on the aperture wheel 118. Because the light has been collimated by the collimator 116, the light entering and leaving an aperture in the aperture wheel 118 has a small spatial cross section. According to one embodiment, the aperture wheel 118 is configured to provide beam diameters of 1.22 mm to 5.5 mm, in twelve approximately equal steps. In some embodiments, these beam diameters translate to spot sizes of 1.0 mm to 6.4 mm, when appropriate contact lenses are used. According to one embodiment, one spot of 500 microns is delivered by the aperture wheel 118 for the treatment of polypoidal choroidal vasculopathy and a range of spots from 1000 to 6400 microns with an average step increment of approximately 400 microns is delivered for PDT. According to one embodiment, the PDT laser provides laser spot sizes smaller than 1 mm for CSC, PCV, CNV, age-related macular degeneration (AMD) or similar indications.

Rather than using one or more lenses to set a spot size, in one embodiment of the invention a single aperture wheel 118 is utilized. This provides costs savings as a metal wheel can be manufactured cheaper than a lens or a zoom system. In addition, aperture wheel 118 is more durable than a lens system and less likely to degrade or become misaligned over time. Further, the aperture wheel 118 is easily interchangeable or replaceable with other aperture wheels. For example, a new series of spot sizes may be utilized by cheaply replacing the aperture wheel 118 having a set of spot size values to another aperture wheel having a different set of spot size values.

According to exemplary embodiments of the invention, the aperture wheel 118 can be configured to provide spot sizes of 500-6000 microns.

Light passes through the aperture wheel 118 to a lens assembly 120. In one embodiment, the lens assembly 120 focuses the image of the aperture wheel 118 to have a 1:1 input/output ratio and projects light to a partially reflective mirror 122. According to one embodiment, the lens assembly 120 comprises two lenses (120a and 120b). The first lens 120a may have a 56 mm focal length (FL) and the second lens 120b may have a 48 mm FL. According to another embodiment, both lenses of the lens assembly 120 may have a 50 mm FL.

Figure 2:
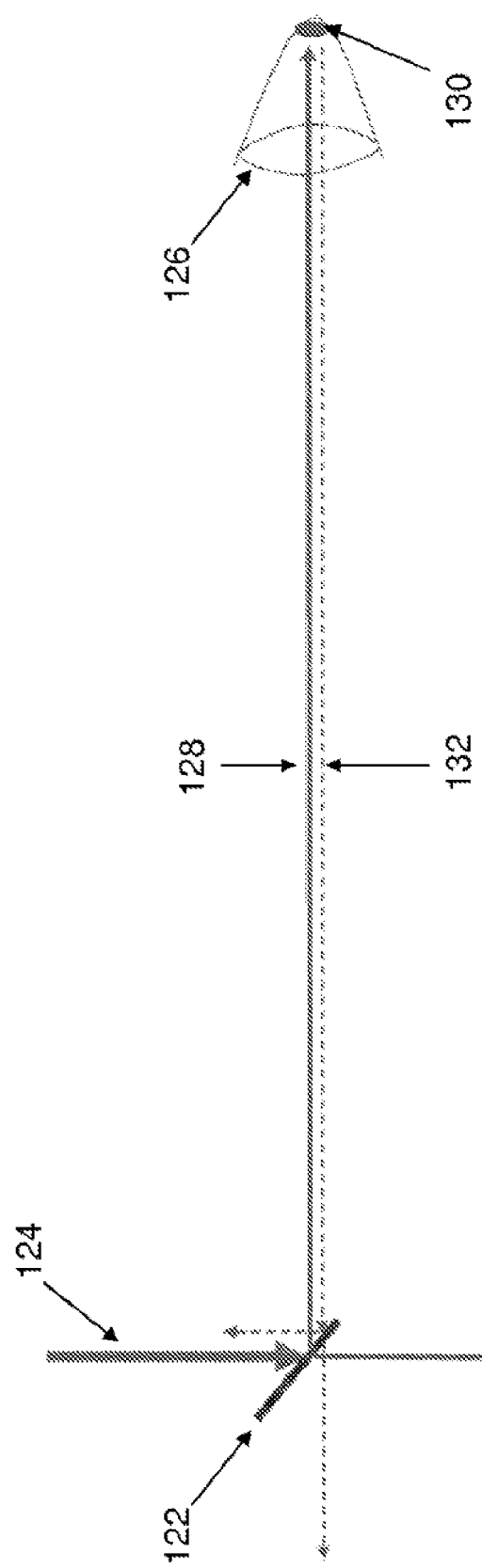
FIG. 2 illustrates an exemplary partially reflective mirror according to one embodiment of the invention.

FIG. 2 illustrates an aiming beam 124 propagated onto an exemplary partially reflective mirror 122 from the lens assembly 120 (FIG. 1). Approximately 50% of the aiming beam 124 is reflected by the partially reflective mirror 122 to the patient's eye 126. Approximately 50% of the aiming beam passes through and is not reflected by the partially reflective mirror 122.

The partially reflected light beam 128 illuminates a target site 130 of the patient's eye 126. A portion of the reflected beam 128 is reflected off the target site 130. Approximately 50% of the light that is reflected off of the target site 130 is again reflected by the partially reflected mirror 122. The other 50% of light reflected off of the target site 130 is transmitted through the partially reflective mirror 122 to the optics of the slit lamp and ultimately to the clinician's eyes. This enables the clinician to see the target site 130 of the patient's eye 126. In some embodiments, the total light emission striking the physician's eye does not exceed safe limits as defined by the *American National Standard for Safe Use of Lasers* (ANSI Z136), the disclosure of which is herein incorporated by reference in its entirety. ANSI Z136 provides safe laser exposure limits for general use. If the laser exposure is below the limits defined by the standard there should be no thermal damage to the retinal tissues due to laser exposure alone.

The partially reflective mirror 122 can act similarly to reflect the treatment beam. For example, the partially reflective mirror 122 can be configured to reflect 90% of the treatment beam. The reflected treatment beam would propagate onto the eye 126 and only a small portion of that beam would be reflected back to the partially reflected mirror 122. 10% of the light from the tissue reflected light would be propagated to the clinician's eyes. The small percentage of the treatment beam ultimately propagated to the clinician's eyes would not be harmful. In some embodiments, the total light emission striking the physician's eye does not exceed safe limits as defined by ANSI Z136, the disclosure of which is herein incorporated by reference in its entirety.

Figure 3:
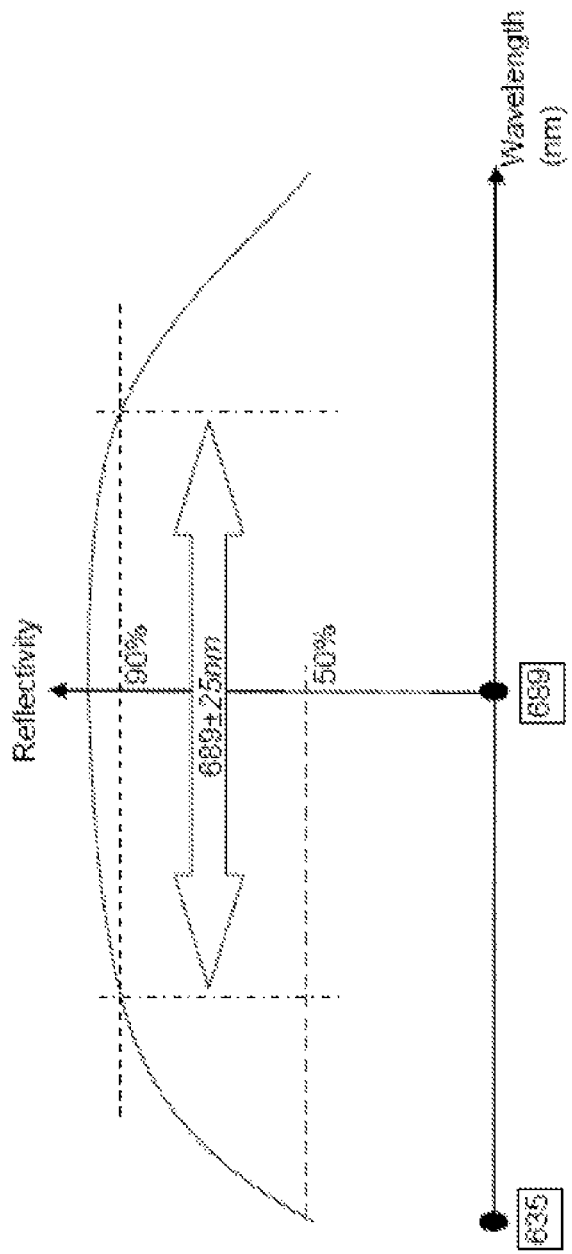
FIG. 3 illustrates an exemplary reflection profile for a partially reflective mirror according to one embodiment of the invention.

FIG. 3 illustrates an exemplary reflective profile for the partially reflective mirror 122. According to an exemplary embodiment, a treatment beam has a wavelength of 689 nm and an aiming beam has a wavelength of 635 nm. Here, the partially reflective mirror 122 would reflect 90% of the treatment beam and 50% of the aiming beam. These figures are exemplary. It is understood that a partially reflective mirror 122 may have any alternative desired reflective profiles.

Figure 4:
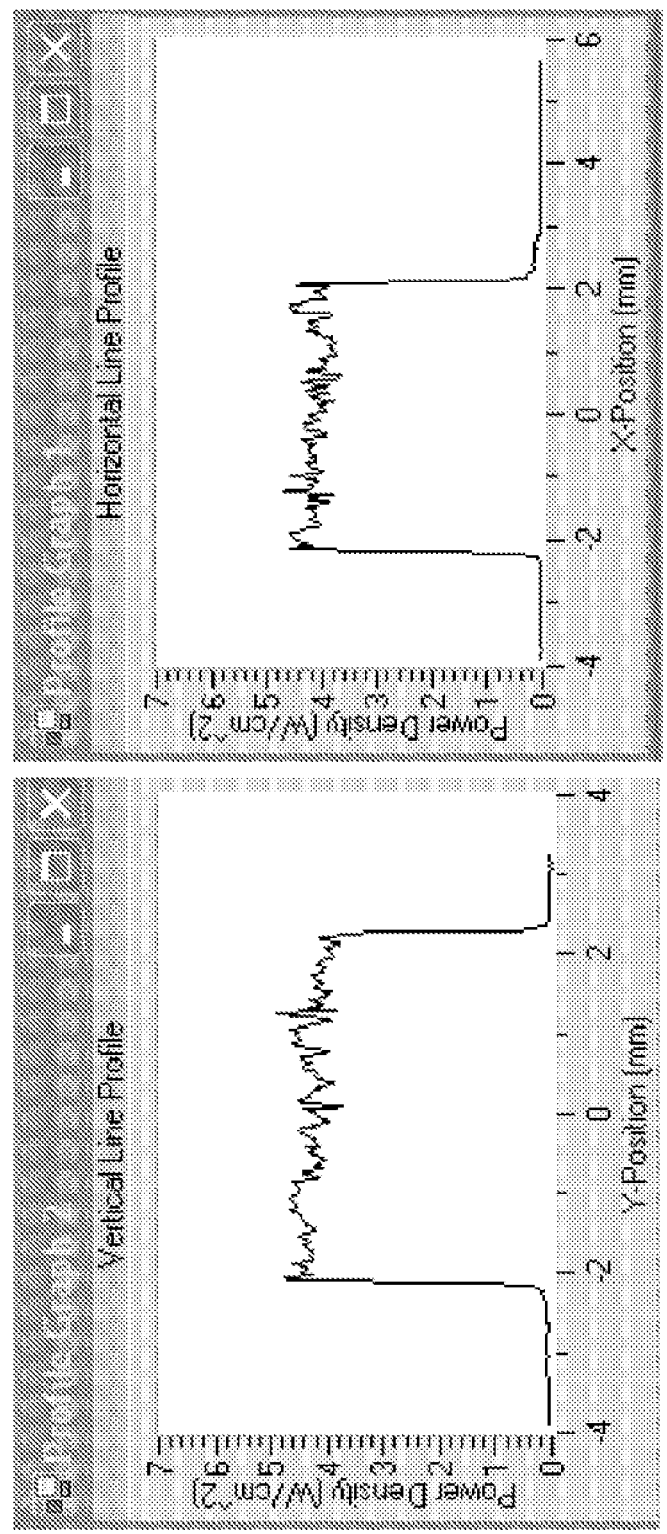
FIG. 4 illustrates an exemplary top hat output profile for a PDT laser according to one embodiment of the invention.

The treatment and aiming light ultimately propagated from the partially reflective mirror 122 to the eye 126 has a top hat beam. A top hat beam is understood in the art and is a laser beam that has a near uniform fluence within a circular disk. FIG. 4 illustrates an exemplary top hat profile for a spot size of 4600 microns for the X and the Y plane that is propagated onto the eye 126. In some embodiments, the PDT laser has a maximum total power of 200 mW for the largest spot size of the laser. However, it is understood that any spot size may be selected to be propagated at any desired power density depending on the desired application. It is further understood that the top hat profile may be optimized for more uniform distribution.

Returning to the exemplary embodiment of FIG. 1, the tonometer post 134 may be used to attach the PDT laser system 100 to a conventional slit lamp microscope. According to one embodiment, the tonometer post 134 is designed to couple to a Haag-Strait or equivalent slit lamp microscope. It is understood that the tonometer post 134 is exemplary and that an equivalent attachment mechanism may be provided to attach the PDT Laser system 100 to a slit lamp microscope or other similar ophthalmic device.

According to an exemplary embodiment, the PDT laser system 100 is mounted on a slit lamp microscope so that the treatment spot is aligned and focused coincident with the slit illumination of a slit lamp.

It is understood that FIG. 1 is provided as an exemplary embodiment and that other components may be added. For example, it is understood that the PDT laser system 100 may be constructed as a stand-alone PDT device with proper casings, removably attachable to a slit lamp microscope, or permanently attached to a slit lamp microscope.

Figure 5:
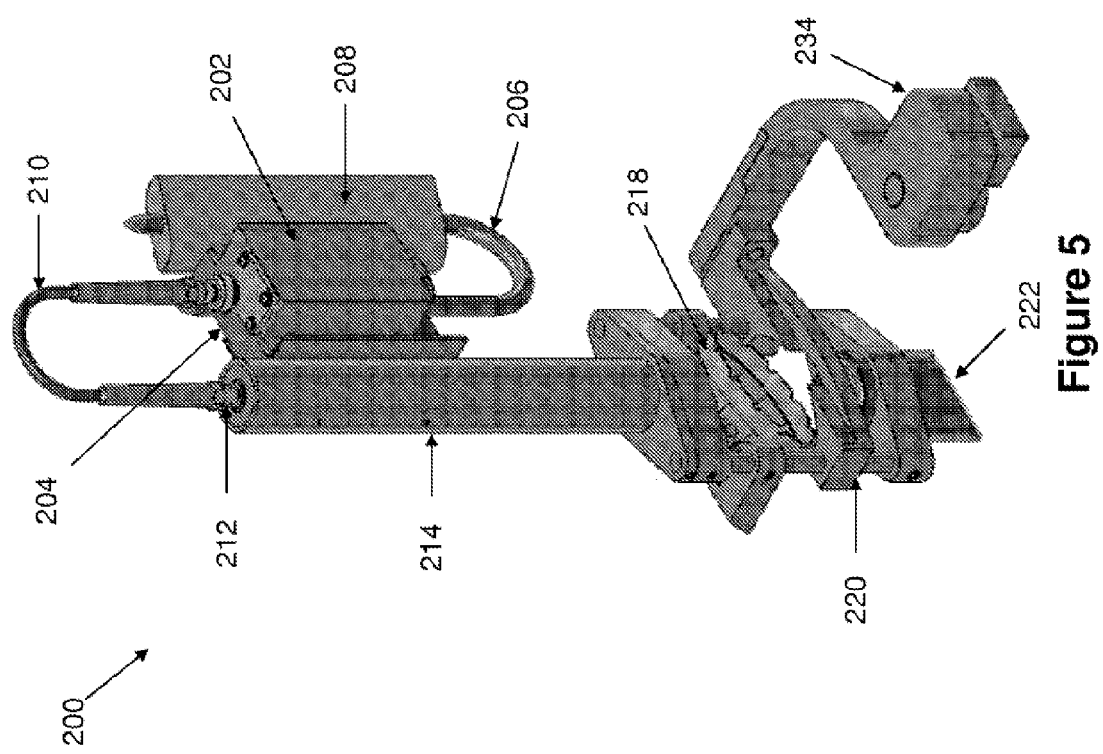
FIG. 5 illustrates the fully assembled internal components of an exemplary PDT laser according to one embodiment of the invention.

FIG. 5 illustrates the fully assembled internal components of PDT laser 200 having a laser head 202, a heat sink 204, a heat pipe 206, a fin array 208, a fiber optic cable 210, an expander 212, a diverger 214, a collimator (not shown), an aperture wheel 218, a lens assembly 220, a partially reflective mirror 222, and a tonometer post 234. In some embodiments, PDT laser 200 comprises the elements of PDT laser 100 discussed above with respect to FIG. 1.

Figure 6:
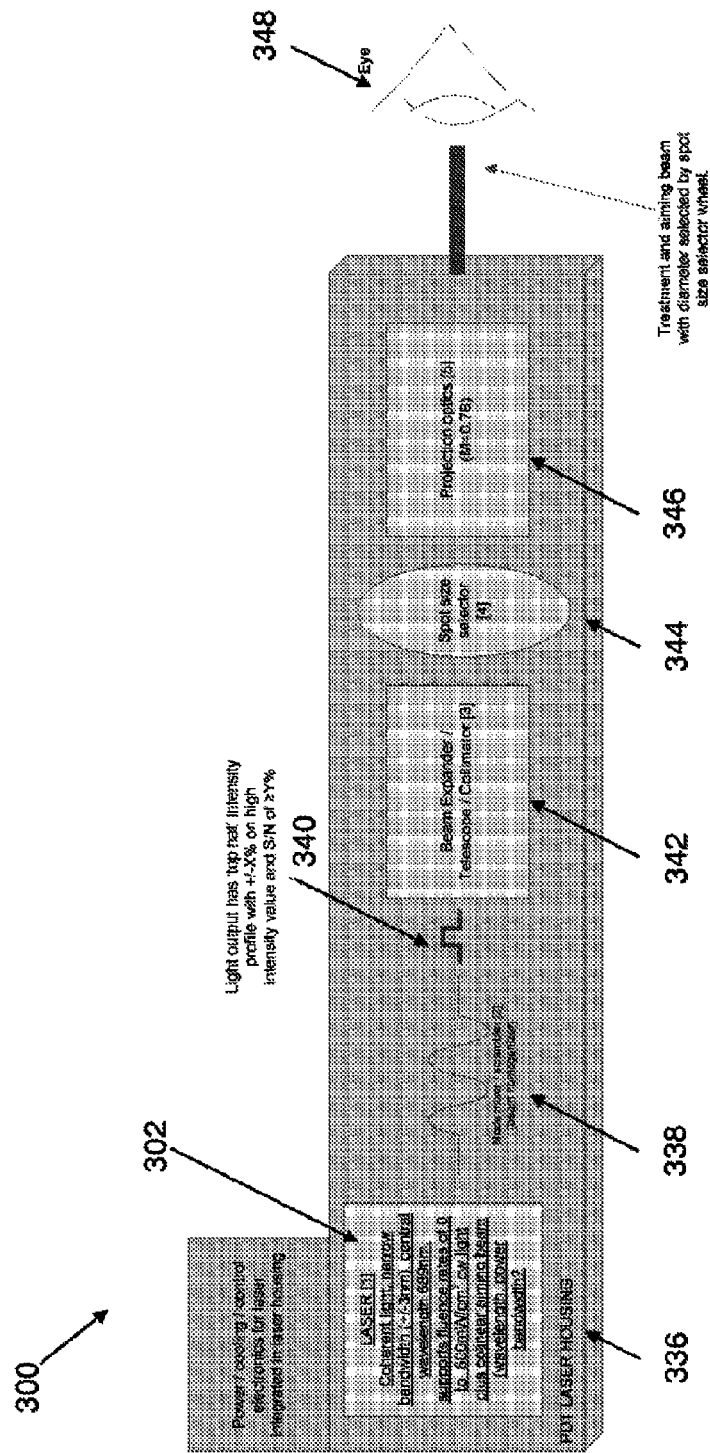
FIG. 6 illustrates a modular view of an exemplary low-cost PDT laser according to one embodiment of the invention.

FIG. 6 illustrates a modular block diagram of exemplary PDT laser in accordance with an embodiment of the invention. PDT laser housing 336 houses a laser head 302. The laser head 302 generates coherent light having a narrow bandwidth of +/−3 mm, a central wavelength of 689 nm, and light that supports a fluence rate of 0 to 600 mW/cm$^2$ light plus a collinear aiming beam. The light from the laser head 302 is provided to the mode scrambler 338. The mode scrambler 338 may be a fiber optic cable or any mode scrambler known in the art. According to one embodiment, the optical modes that occur when a laser beam is transmitted by a multi-mode fiber optic are scrambled in the mode scrambler 338 to generate a circular beam with a top hat intensity profile. According to one embodiment, the laser head 302 may be a laser diode that combines the laser treatment beam and the aiming beam so that their laser outputs are optically collinear with regard to the mode scrambler 338.

The light output 340 from the mode scrambler 338 has a top hat intensity profile that propagates to the beam expander/telescope/collimator 342. According to one embodiment, the top hat intensity profile is desirable because it provides a very uniform optical fluence rate (mW/cm$^2$) across the laser beam cross-sectional area to provide uniform activation of a photosensitizer across the area of tissue being treated.

According to one embodiment, the laser beam from the mode scrambler 338 is expanded from 400 microns to 12 mm in diameter. The collimated light from the expander/telescope/collimator 342 pass collimated light having a 12 mm diameter to the spot size selector 344.

According to one embodiment, the spot size selector 344 may be machined with a plurality of spot size holes. The spot size selector 344 may be manually rotated so that one spot size is selected at a time. When the spot size is selected, the hole intersects with the expanded laser beam and the laser light is transmitted through the hole onto projection optics 346. According to one embodiment, spot sizes in the range of 1.0 mm to 6.4 mm may be produced on the retina to treat lesion diameters from 0 to 5.4 mm. It is understood that a varying range of spot sizes may be used as known in the art.

The light passes through the spot size selector 344 to the projection optics 346 wherein the projection optics provide a magnification factor (M) of 0.78. It is understood that a varying range of M may be used as known in the art. The light is projected from the projection optics 346 to the eye 348 to excite a photosensitizing agent.

Figure 7B:
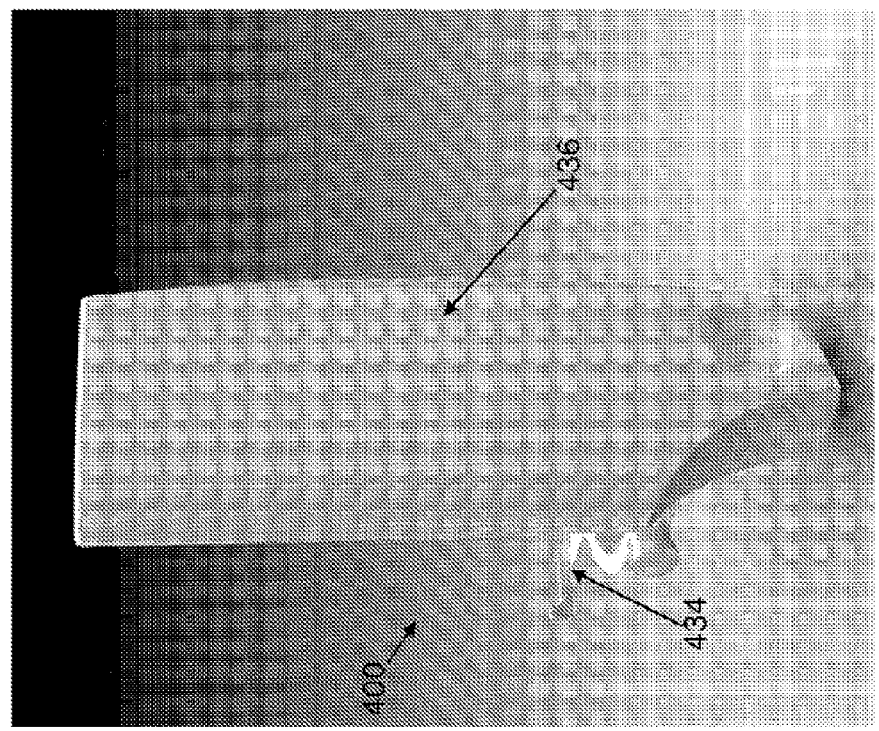
FIGS. 7(a)-(b) illustrate an exemplary PDT laser having a housing according to one embodiment of the invention.
Figure 7A:
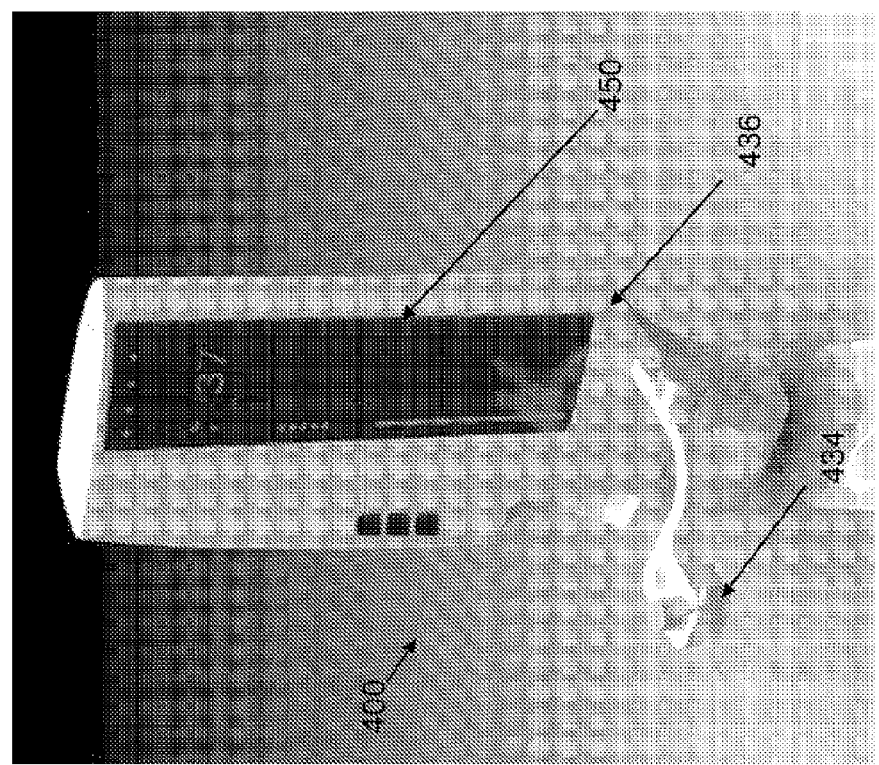

FIG. 7(*a*) illustrates an exemplary PDT laser system 400 having a housing 436 and a tonometer post 434. The housing 436 has a display 450 that can display various treatment and laser parameters. According to one embodiment, the display 450 shows the therapeutic count down time: 83 seconds to 0. FIG. 7(b) illustrates a profile view of an exemplary embodiment of the PDT laser system 400.

Figure 8:
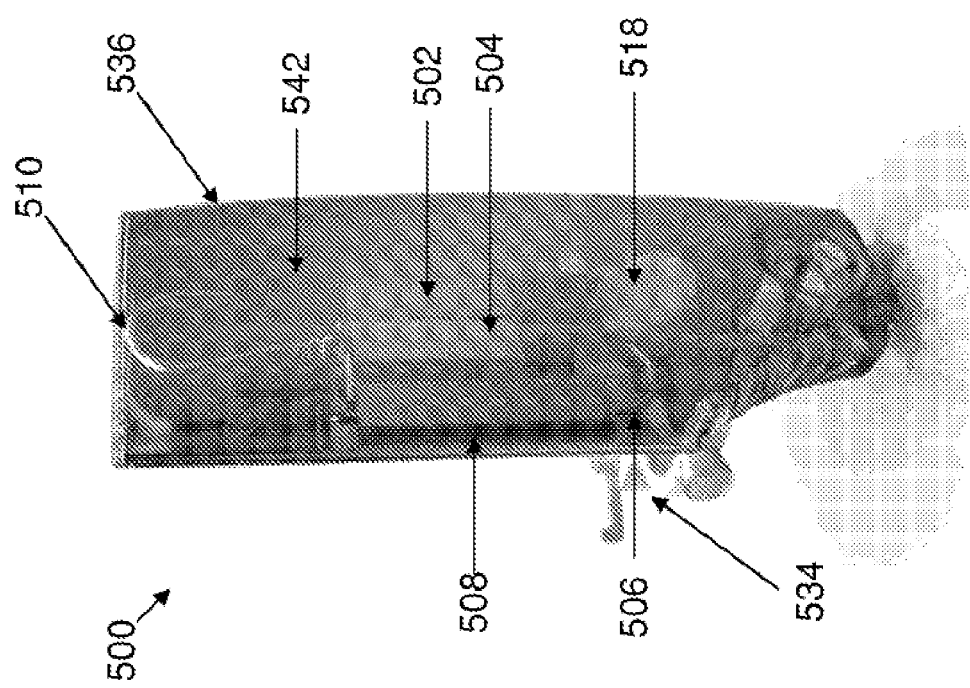
FIG. 8 illustrates an exemplary PDT laser having a portion of the housing made transparent for illustrative purposes according to an embodiment of the invention.

FIG. 8 illustrates a side view of an exemplary PDT laser system 500, with the housing made transparent for illustrative purposes. A tonometer post 534 is provided on the outside of the housing 536. Inside the housing 536, a laser head 502 generates a treatment and an aiming beam that is propagated through a fiber optic cable 510. The fiber optic cable 510 scrambles the modes. A beam expander/telescope/collimator 542 expands and collimates the light. An aperture wheel 518 selects an aperture size from the light from the expander/telescope/collimator 542. The light from the aperture wheel 518 is propagated through a lens assembly (not shown) onto the partially reflected mirror to an eye (not shown). Heat is dissipated from the laser head 502 through the heat sink 504, heat pipe 506, and the fin array 508.

Figure 9:
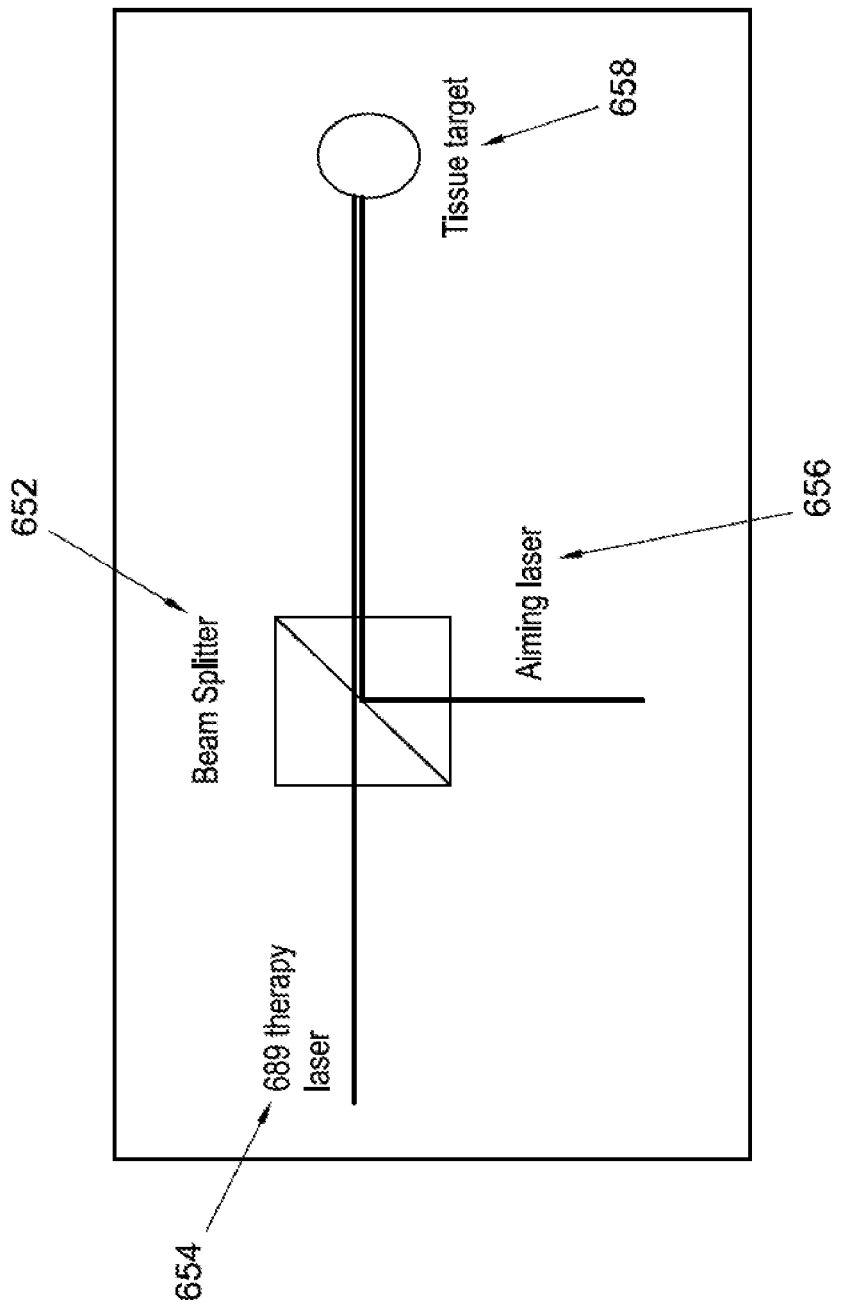
FIG. 9 illustrates an exemplary beam splitting system to provide coincident treatment and aiming lasers according to an embodiment of the invention.
Figure 10:
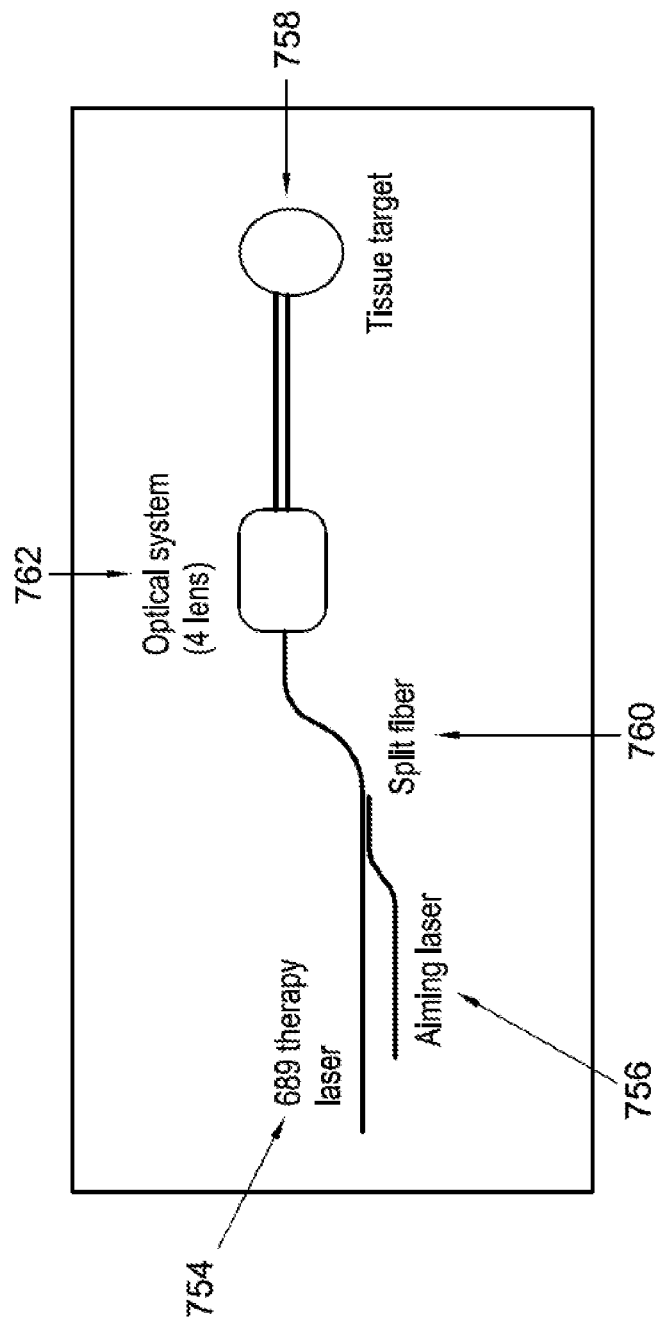
FIG. 10 illustrates an exemplary split fiber system to provide coincident treatment and aiming lasers according to an embodiment of the invention.
Figure 11:
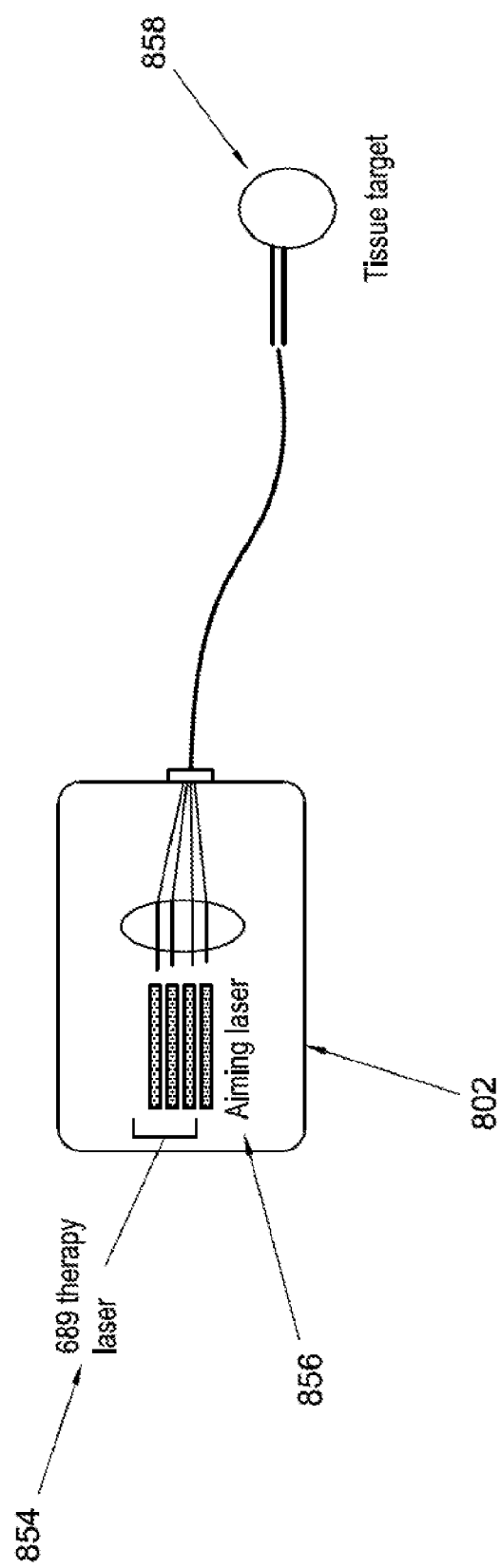
FIG. 11 illustrates an exemplary laser bar system to provide coincident treatment and aiming laser beams according to an embodiment of the invention.

FIGS. 9, 10, and 11 illustrate exemplary optical configurations to provide a coincident aiming and laser beam. FIG. 9 illustrates a beam splitter 652 that combines a 689 nm therapy laser 654 and an aiming laser 656 to a tissue target 658. FIG. 10 illustrates a 689 nm therapy laser 754 and an aiming laser 756 that are combined in a split fiber 760. The split fiber 760 delivers the two beams to an optical system 762 having four lenses that propagates the light to the tissue target 758. FIG. 11 illustrates a laser head 802 that generates a 689 nm therapy laser 854 and an aiming laser 856 that is propagated through a fiber optic cable to a tissue target 858. It is understood that the therapy or aiming laser beams (654, 754, and 854) described herein may be of any desired wavelength as known in the art.

It is understood that the optical system 762 may be configured as described in previous embodiments or in any other method known in the art. It is further understood that the optical system 762 may have any number of lenses. It is understood that the systems and methods described herein to provide coincident aiming and treatment beams are merely exemplary and that any method known in the art may be utilized to provide coincident treatment and aiming beams.

Figure 12:
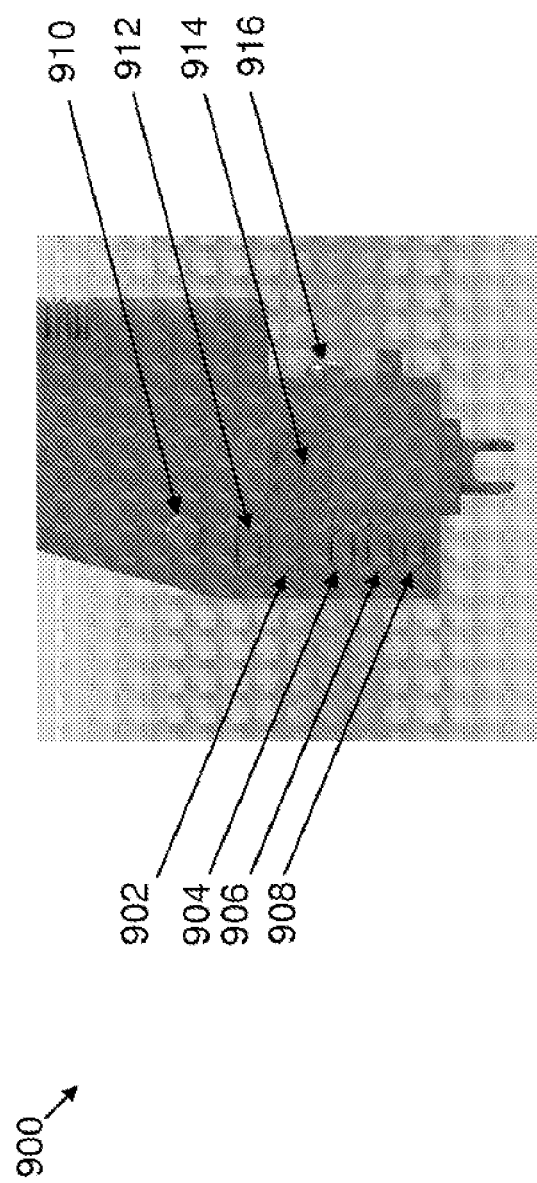
FIG. 12 illustrates an exemplary user interface that enables an operator to setup a laser and perform therapy therewith.

FIG. 12 illustrates an exemplary user interface 900 that enables an operator—such as a physician, an ophthalmologist, a clinician, etc.—to setup a laser and perform therapy therewith, such as the lasers described herein. User interface 900 includes a display 902, a contact lens selector 904, a fluence rate selector 906, an aiming beam intensity selector 908, an emergency stop 910, a laser state selector 912, a spot size selector 914, and a key switch 916.

In some embodiments, display 902 is a two digit display that displays a treatment countdown, provides feedback when the fluence rate is changed and displays error codes when required. The display may provide a countdown from 83 seconds when the laser is fired and, in some embodiments, the countdown cannot be altered except by restarting the laser system.

Figure 14:
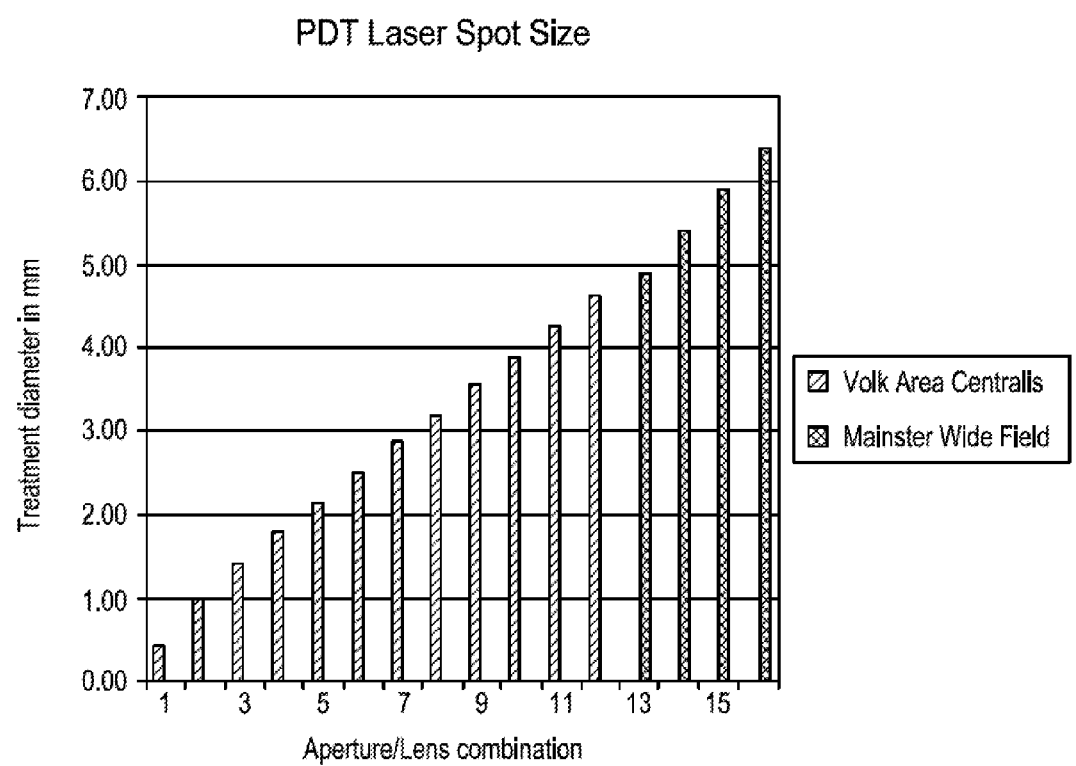

Contact lens selector 904 may provide for toggling between available contact lens magnifications. For example, contact lens selector 904 may toggle between a 1.06× contact lens magnification (corresponding to a Volk Area Centralis contact lens or equivalent) and a 1.47× contact lens magnification (corresponding to a Mainster Wide Field contact lens or equivalent). FIGS. 13 and 14 illustrate some exemplary combinations of aperture size, spot size, and system magnification, in accordance with one embodiment of the invention. It will be understood by one of ordinary skill in the art that other combinations of spot sizes, system magnification, and apertures sizes could be equivalently used without deviating from the scope of the invention.

According to one embodiment, fluence rate selector 906 allows the physician to select the desired fluence rate. When pressed while the laser is in setup mode, this button cycles the system through fluence rates of 600, 450, 300 or 150 mW/cm$^2$. When the fluence rate is changed, the display will read 60, 45, 30 or 15, signifying 600, 450, 300 or 150 mW/cm$^2$. When a 600 mW/cm$^2$ is selected as the fluence rate, a green LED shows beside the fluence rate selector. When a fluence rate other than 600 mW/cm$^2$ is selected as the fluence rate, a red LED shows beside the fluence rate selector. It is to be understood that the settings of the fluence rate selector 906 and corresponding display of LEDs may be varied without deviating from the scope of the invention.

In some embodiments, aiming beam intensity selector 908 allows for continuous adjustment of the aiming beam from a minimum of 0 mW to a maximum of <1 mW output.

According to one embodiment, emergency stop 910 is a latching switch that will immediately disable power to the entire unit. A restart of the system will occur when the switch is "unlatched" and it will return to default settings.

Laser state selector 912 may be adjusted to one of a ready state or a stand-by state. In both states the aiming beam is on. However, only in the ready state can the treatment beam be activated. When the laser is in "ready" mode a green LED shows beside the laser state selector. When the laser is in "standby" mode a red LED shows beside the laser state selector.

According to one embodiment, spot size selector 914 is rotated to select the laser beam spot size.

Key switch 916 may be a main power switch. When this key switch is turned to the "on" position, the laser powers up and the aiming beam is enabled. Whenever the key is turned on, the system defaults to standard parameters of 600 mW/cm$^2$, 83 second treatment timing, and 1.06× contact lens magnification. If required, the key can be removed from the switch when the system is in the "off" mode providing a simple way to control access to the laser system.

Although not illustrated in FIG. 12, the laser system may include other components, such as a foot switch and other controls and indicators. A foot switch may activate the treatment beam when the laser is in "ready" mode. If the foot switch is released, the treatment beam is deactivated. If the treatment beam is interrupted during use by releasing the foot switch, the 83 second countdown will stop. If the foot switch is activated again without first shutting down the laser system, the countdown will resume from where it left off. Other controls may include a remote interlock connector that prevents operation of the treatment beam when the terminals of the connector are not electrically joined and an audible signal to indicate that the treatment beam is being fired.

Figure 15:
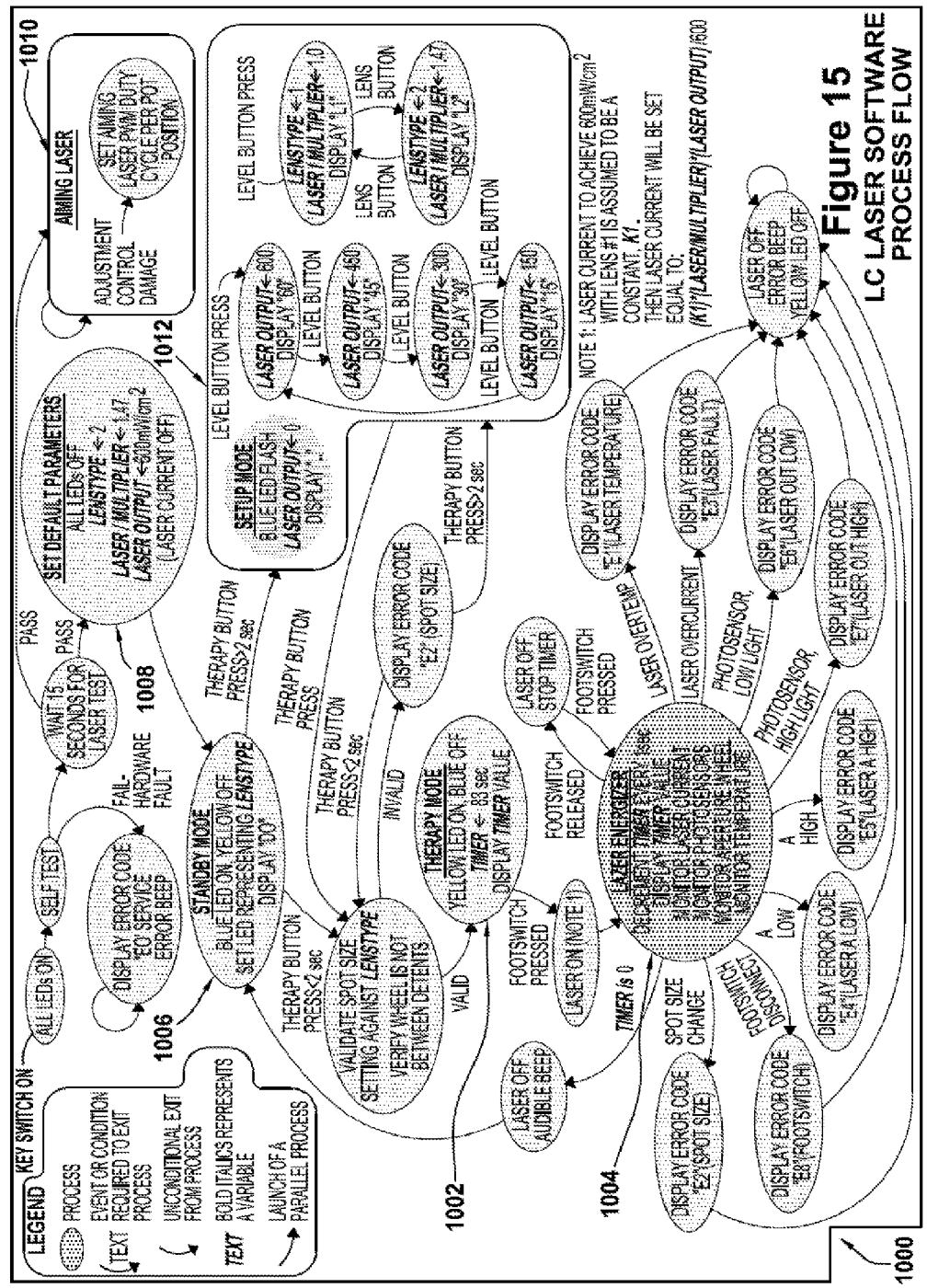
FIG. 15 illustrates an exemplary process flow carried out by software or other circuitry to execute steps for performing a laser-based therapy treatment, such as the treatments described herein.

FIG. 15 illustrates an exemplary process flow 1000 carried out by software or other circuitry to execute steps for performing a laser-based therapy treatment, such as the treatments described herein. Process flow 1000 includes a therapy mode process 1002, a laser energized process 1004, a standby mode process 1006, a set default parameters process 1008, an aiming laser process 1010, and a setup mode process 1012. Each process in process flow 1000 includes arrows indicating an event or condition required to exit the process, an unconditional exit from a process, variables, and launches of parallel processes.

The following exemplary method of system setup may be performed in conjunction with process flow 1000 above: (1) attach the laser unit to the slit lamp (SL) and align the SL observation system and illumination system, (2) turn laser unit power on using key switch, (3) allow the laser unit to self-test for approximately 15 seconds, (4) place the focusing post in the SL and bring it into focus while looking through the SL binoculars and having a narrow slit beam illumination, and (5) adjust the laser unit's lever and focusing knob, to ensure that the laser is aligned and focused at the same location as the slit beam.

The following exemplary method of system standby may be performed in conjunction with process flow 1000 above: (1) power-up laser and laser defaults to a standard treatment using 600 mW/cm$^2$ 83 second timing and a 1.06× contact lens, (2) if a standard treatment is desired, follow standard treatment method (see below), (3) if a non-standard treatment is desired: (3a) depress and hold the bottom button (see FIG. 12) until the green led flashes, the display will indicate '00' and (3b) using the upper button (see FIG. 12), alternate fluence rates may be selected (either 600, 450, 300 or 150 mW/cm$^2$—pressing the button will cycle the fluence rates through the available options and the display will indicate 60, 45, 30 or 15 signifying 600, 450, 300 or 150 mW/cm$^2$.)

The following exemplary method of standard treatment method may be performed in conjunction with process flow 1000 above: (1) place the laser in ready mode by pressing the upper button (see FIG. 12), (2) adjust the intensity of the aiming beam as desired, (3) adjust the spot size (if spot sizes larger than 4.5 mm are required, change the contact lens magnification factor to 1.47×), (4) activate the laser (for example, using a foot pedal), (5) keep foot pedal pressed (counter will run from 83 seconds and at 0 an audible beep will sound, at which time both the aiming and treatment beams will be shutdown).

In some embodiments, additional safety measures may be added. In some embodiments, a latching emergency stop switch can immediately disable power to the entire unit. In one embodiment, the control unit monitors the therapeutic laser during activation, ensuring that the wavelength and power levels remain within the set parameters during treatment. In other embodiments, a watchdog feature ensures that, in case of failure of the control unit, the system will be shut down. According to one embodiment, maximum output of the laser is set in the circuit design, preventing excessive laser output in the case of simultaneous control unit and watchdog failure. In some embodiments, a door interlock is provided that prevents use of the treatment beam if the operating room door is opened.

In some embodiments, a bar code scanner is added to a laser system to allow clinicians to quickly setup the system to correspond to the treatment parameters of one or more photoactivating drugs. For example, a vial of a photoactive drug (such as Visudyne®, for example) may be equipped with a bar code identifying the drug within the vial. In one embodiment, the bar coding system incorporates a radio frequency identification system ("RFID") that gathers information from a RFID tag on the vial. In some embodiments, the laser system may be preprogrammed with the identified photoactive drug's treatment parameters. In those embodiments, simply identifying the drug may be sufficient. In other embodiments, the bar code or RFID tag may include other information such as the exact treatment parameters, expiration date of the drug, etc. Once the treatment parameters of the identified drug are determined, the laser system may automatically alter the beam wavelength, fluence rate, power, duration of treatment, etc. accordingly. In some embodiments, the laser system may require additional physical changes to correspond to a particular photosensitive drug, such as replacing the partially reflective mirror. In some embodiments, the bar coding system and associated circuitry are stored in the laser housing. In some embodiments, the bar coding system may be housed separately. Some further embodiments may include an approval system on the laser system that requests user confirmation before adjusting the laser system treatment parameters. In some embodiments, the laser system is configured to read treatment parameters of all PDT compounds. In some further embodiments, the bar coding system is configured to read treatment parameters from one or more of a vial, a box, a reference book, and a electronic display. Such electronic displays can be a smart phone or a computer or any other electronic display and the information may be gathered from an email, a PDT compound manufacturer's website, or a database, for example.

Figure 16B:
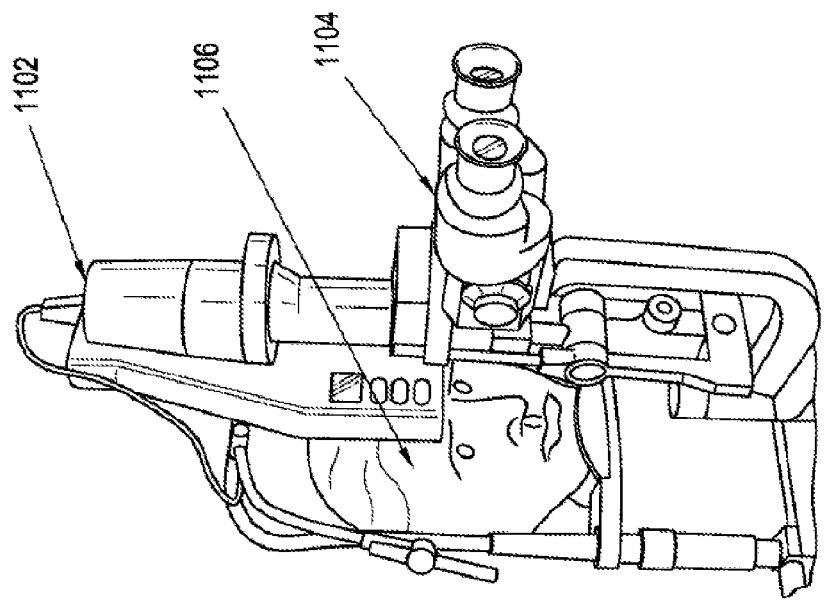
FIGS. 16(a) and 16(b) illustrate an exemplary PDT laser according to an embodiment of the invention, mounted on a slit lamp, with a mannequin's head at the position of the patient's head.
Figure 16A:
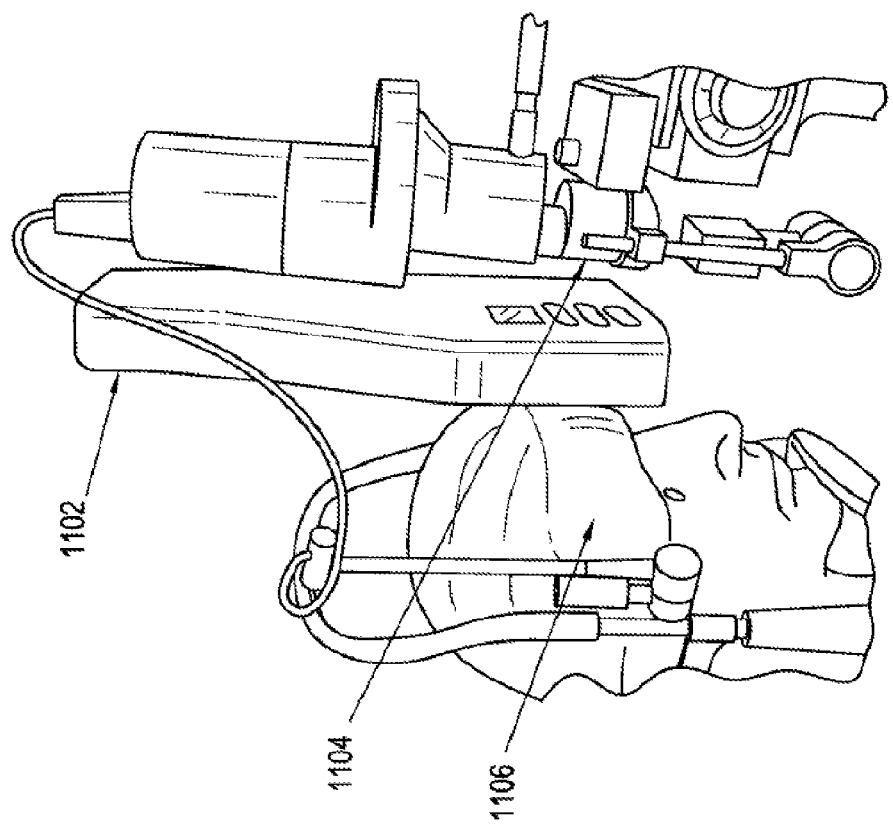

FIGS. 16(*a*) and 16(*b*) illustrate an exemplary PDT laser 1102 according to an embodiment of the invention, mounted on a slit lamp 1104, with a mannequin's head 1106 at the position of the patient's head. PDT laser 1102 may comprise any of the PDT laser's described herein. The slit lamp 1104 may comprise any slit lamp which has structure to receive exemplary PDT laser 1102.

The following is a description of an exemplary working example utilizing one or more embodiments of the disclosed invention. Patient I is treated with a regimen in which they are administered 6 mg/M$^2$ (of body surface area) of verteporfin in a commercially available liposomal intravenous composition obtainable from QLT PhotoTherapeutics, Vancouver, BC, assignee of the present application. Administration is intravenous. Thirty minutes after the start of infusion, the patient is administered a laser light having a wavelength of about 689 nm at 150-600 mW/m$^2$. Patient II is administered 6 mg/M$^2$ of verteporfin in the liposomal formulation, intravenously as with Patient I, but the laser light begins 20 minutes after the start of infusion. Patient III is subject to a regime identical to Patient I except 12 mg/M$^2$ of verteporfin is administered.

Although individual components have been described herein, it is understood that any component known in the art may be used to accomplish the same or similar function.

It is understood that an ocular lens such as Mainster, Volk Area Centralis, or any other indirect image lens known in the art may be utilized to aid in PDT or other treatments. These ocular lenses are required to focus the laser on the back of the retina. Without the ocular lenses the fundus cannot be visualized and the laser beam cannot be focused to the expected area on the patient's retina. It is further understood that any indirect (real) image contact lens may be utilized for PDT.

It is understood that many unlabeled portions of the figures may represent common mechanical connectors or pieces and are representative of any mechanical connector or piece known in the art.

It is understood that the invention is not limited to PDT and may be configured to be utilized in other photocoagulation or non-thermal procedures (e.g., transpupillary thermotherapy). It is further understood that the invention may be utilized for the treatment of central serous chorioretinopathy (CSC) or polypoidal chorodial vasculopathy (PCV), subfoveal occult or classical) coroidal neovasculzation (CNV), age-related macular degeneration (AMD). It also understood that principles of embodiments of the invention could be expanded to include thermal treatments.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described, but instead can be applied, alone or in some combination, to one or more of the other embodiments of the invention, whether or not such embodiments are described and whether or not such features are presented as being a part of a described embodiment. Thus the breadth and scope of the present invention should not be limited by any of the above-described exemplary embodiments.

What is claimed is:

1. A laser system configured for administering therapy to a patient comprising:
    a laser source operable to emit a first laser beam operating a first wavelength and a second laser beam operating a second wavelength, wherein the laser source operates at 1.5 watts or less;
    a passive cooling system, wherein the passive cooling system comprises a heat pipe, a heat sink, and a fin array;
    a fiber optic cable coupled to the laser source and configured to guide and homogenize the first and second laser beams;
    a first optical system coupled to the fiber optic cable and configured to increase the diameter of and collimate the first and second laser beams;
    a spot-size selector coupled to the first optical system and comprising a plurality of apertures; and
    a second optical system coupled to the spot-size selector and configured to focus the first and second laser beams on an eye tissue of the patient.

2. The laser system of claim 1, further comprising an optical filter configured to partially reflect the first and second laser beams, wherein the optical filter reflects a first percentage of the first laser beam and a second percentage of the second laser beam, the first percentage being greater than the second percentage.

3. The laser system of claim 2, wherein the laser system is contained within a single housing.

4. The laser system of claim 3, wherein the housing is configured to be attached to a slit-lamp microscope.

5. The laser system of claim 1, wherein the fiber optic cable has a diameter of approximately 350 to 450 microns and a length of approximately 200 to 300 millimeters.

6. A method of activating a photoactive drug administered to a patient intravenously using a laser system according to claim 1, comprising:
    activating the photoactive agent with the first laser beam generated by the laser source, the first laser beam having a first wavelength;
    generating the second laser beam operating at a second wavelength, wherein the combined power levels of both the first and second laser beams are 1.5 watts or less;
    passively cooling the laser source by coupling the heat sink to the laser source;
    guiding the first and second laser beams through the fiber optic cable coupled to the laser source, wherein the fiber optic cable homogenizes the first and second laser beams;
    increasing the diameter of and collimating the first and second laser beams;
    adjusting a spot-size of the first and second laser beams; and
    focusing the first and second laser beams on an eye tissue of the patient; wherein at least the first laser beam activates the photoactive drug within the patient's eye tissue to provide therapy to the patient.

7. The method of claim 6, wherein the photoactive drug comprises verteporfin.

* * * * *